United States Patent
Kocher et al.

(10) Patent No.: US 11,678,806 B2
(45) Date of Patent: Jun. 20, 2023

(54) PERSONAL WARNING TEMPERATURE

(71) Applicant: Ideal Innovations Incorporated, Arlington, VA (US)

(72) Inventors: Robert William Kocher, McLean, VA (US); Douglas Earl Dyer, Herndon, VA (US); John Shelly Bowling, II, Reston, VA (US)

(73) Assignee: Ideal Innovations, Inc., Arlington, VA (US)

( * ) Notice: Subject to any disclaimer, the term of this patent is extended or adjusted under 35 U.S.C. 154(b) by 0 days.

(21) Appl. No.: 17/857,111

(22) Filed: Jul. 4, 2022

(65) Prior Publication Data

US 2022/0330834 A1 Oct. 20, 2022

Related U.S. Application Data

(60) Continuation of application No. 17/094,236, filed on Nov. 10, 2020, now Pat. No. 11,375,903, which is a division of application No. 16/986,359, filed on Aug. 6, 2020, now Pat. No. 11,224,345.

(51) Int. Cl.
*A61B 5/01* (2006.01)
*G16H 50/30* (2018.01)
*A61B 5/00* (2006.01)
*G16H 40/67* (2018.01)

(52) U.S. Cl.
CPC ............... *A61B 5/01* (2013.01); *A61B 5/486* (2013.01); *G16H 40/67* (2018.01); *G16H 50/30* (2018.01); *A61B 2562/0271* (2013.01)

(58) Field of Classification Search
None
See application file for complete search history.

(56) References Cited

U.S. PATENT DOCUMENTS

| | | | |
|---|---|---|---|
| 6,821,249 B2 | 11/2004 | Casscells, III | |
| 10,872,694 B2 | 12/2020 | Maeta | |
| 11,224,344 B2* | 1/2022 | Ellis | A61B 5/02055 |
| 2010/0152606 A1* | 6/2010 | Menashe | G01K 3/00 |
| | | | 600/549 |

(Continued)

OTHER PUBLICATIONS

Archived Pfizer Webpage (Year: 2022).*
International Search Report and Written Opinion for App. No. PCT/US2021/045069, dated Nov. 8, 2021, 7 pages.

*Primary Examiner* — Benjamin S Melhus
(74) *Attorney, Agent, or Firm* — Butzel Long; Donald J. Lecher

(57) ABSTRACT

The Personal Warning Temperature (PWT) is a method of determining a person's personal warning temperature that defines a fever for that person. The PWT may also be used to provide an indication to recommend medical evaluation for a person. The method includes analyzing a person's body temperature measurements taken over time when the person may be healthy, in order to find the person's average temperature, a standard deviation, a channel defined by an upper and lower temperature bound using the average and standard deviation, such that nearly all body temperatures fall within the channel, and a personal warning temperature similarly defined using the average, and the standard deviation. A personal warning temperature may be used for improved and accelerated awareness of a person's health status.

15 Claims, 10 Drawing Sheets

(56) References Cited

U.S. PATENT DOCUMENTS

| | | |
|---|---|---|
| 2013/0278414 A1 | 10/2013 | Sprigg |
| 2014/0266694 A1 | 9/2014 | McCluskey |
| 2014/0298859 A1* | 10/2014 | Balboni ................ G01K 1/024 |
| | | 63/1.13 |
| 2018/0055457 A1* | 3/2018 | Balboni ................ G01K 13/20 |
| 2019/0021701 A1 | 1/2019 | Vardi |
| 2019/0350535 A1 | 11/2019 | Zhao |
| 2020/0196962 A1 | 6/2020 | Zhao |
| 2020/0268341 A1* | 8/2020 | Stroman ................ A61B 7/04 |
| 2021/0186399 A1* | 6/2021 | Gunderson ........... A61B 5/1116 |
| 2021/0307636 A1* | 10/2021 | Botsford ................ G01R 23/16 |
| 2021/0391088 A1* | 12/2021 | Harrah ................... A61B 5/01 |

* cited by examiner

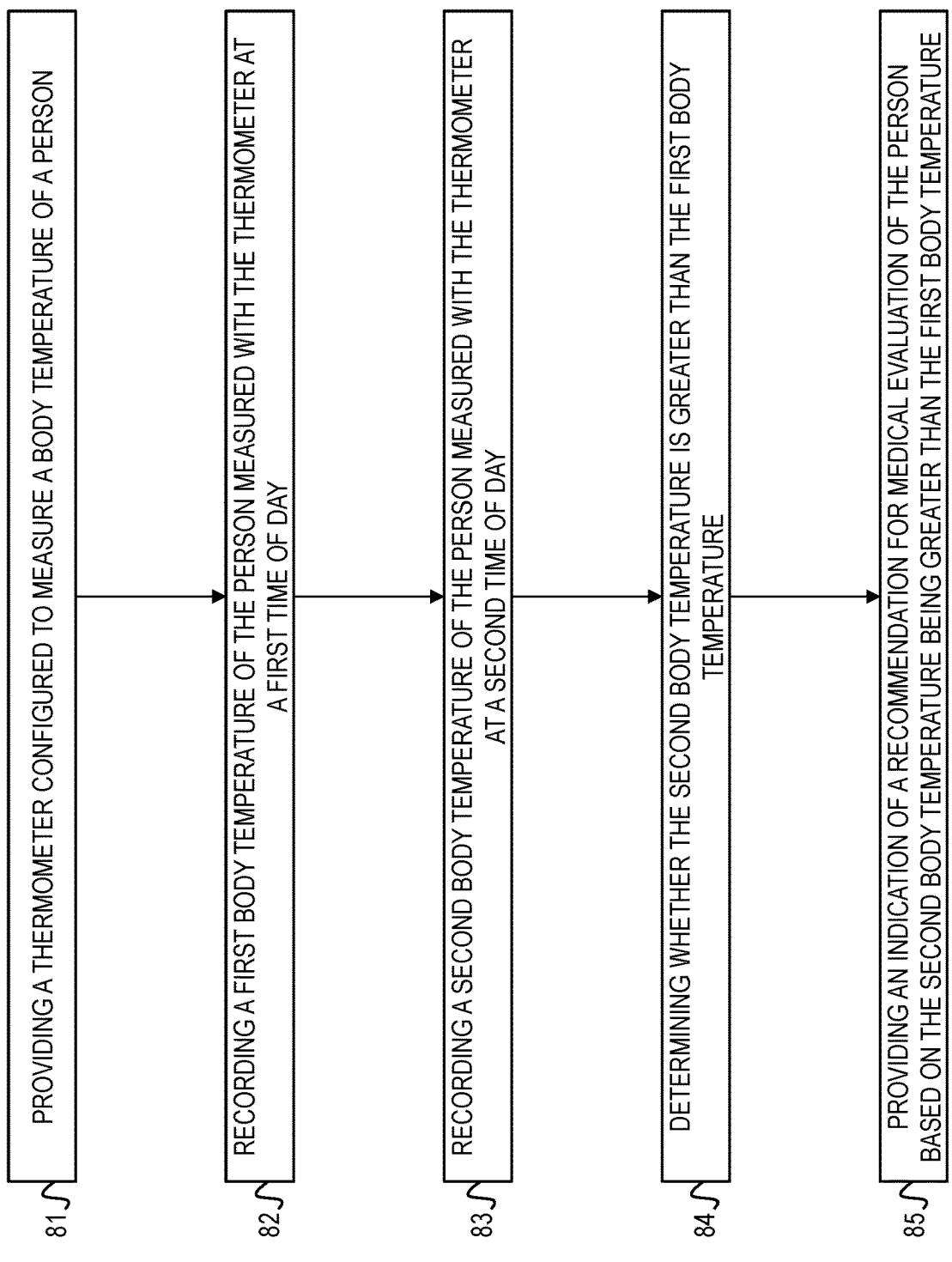

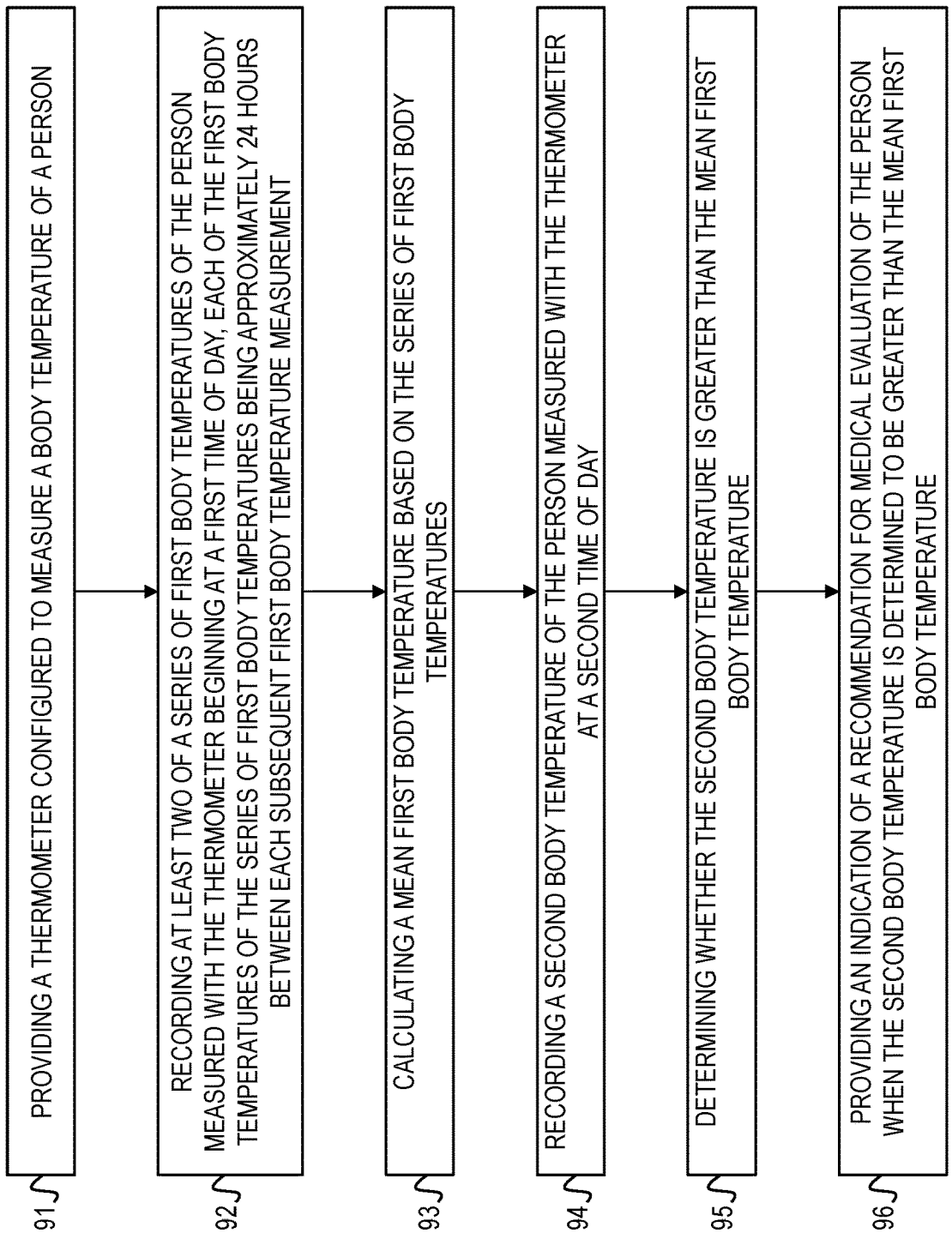

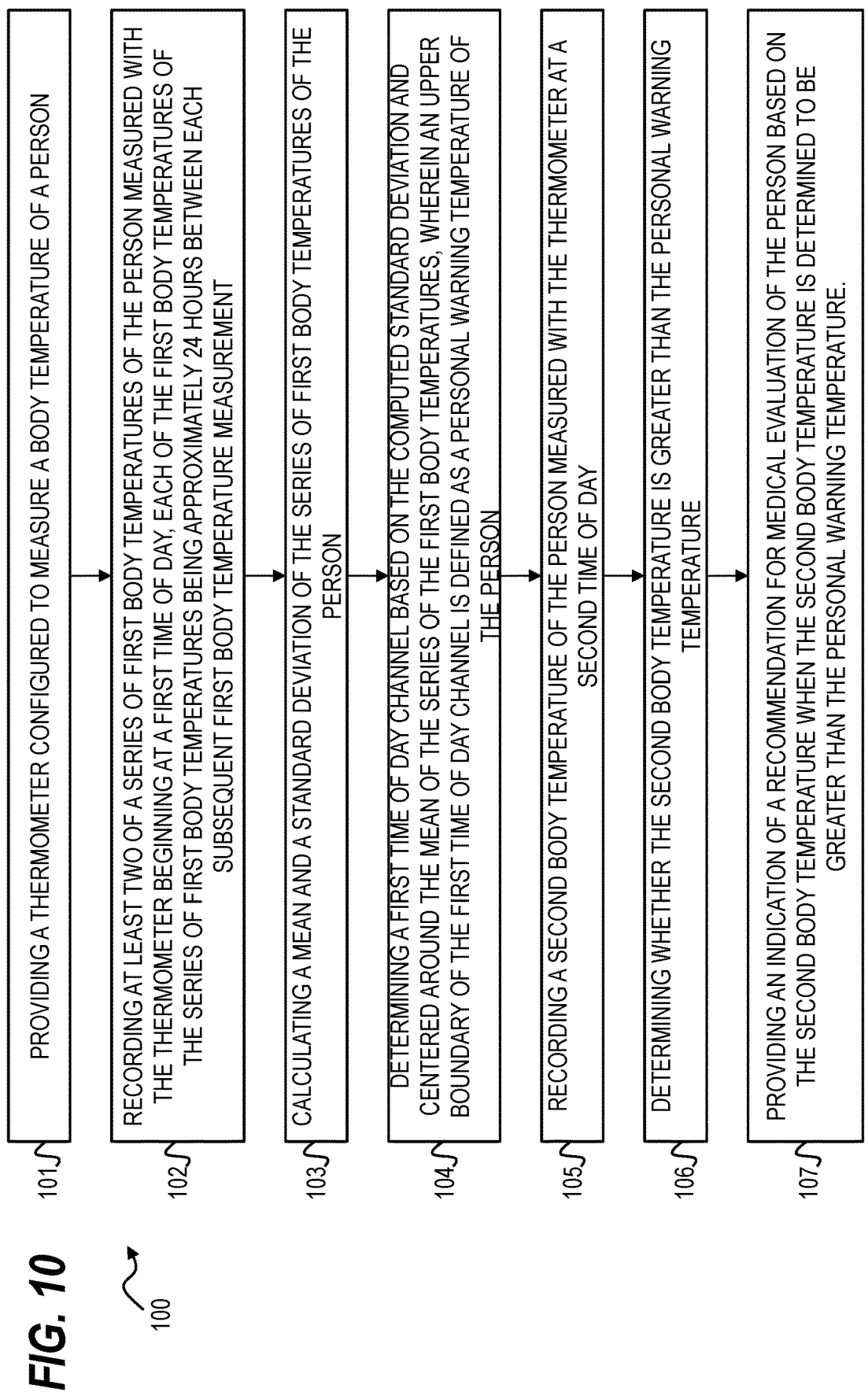

PERSONAL WARNING TEMPERATURE

CROSS-REFERENCE TO RELATED APPLICATIONS

This continuation-in-part patent application claims priority to U.S. patent Ser. No. 17/094,236, filed on Nov. 10, 2020 and issued as U.S. Pat. No. 11,375,903 on Jul. 5, 2022, being a divisional application of U.S. patent Ser. No. 16/986,359, filed on Aug. 6, 2020 and issued as U.S. Pat. No. 11,224,345 on Jan. 18, 2022. The priority applications are incorporated herein, in their entirety.

BACKGROUND OF THE INVENTION

Field of Invention

The invention relates to the field of medical screening and health monitoring; and particularly to reduce the spread of COVID-19 and other infectious diseases. The invention reduces or prevents the spread of infectious diseases by enabling the early detection of body temperature abnormalities based on personal warning temperatures that are otherwise not noticed by widely accepted minimum temperature thresholds for identification of fever.

Description of the Related Art

Fever may be defined as having a body temperature above the normal range. When a person is healthy, body temperature naturally varies for a variety of factors such as sex, time of day, current metabolic activity, ambient temperature, and biological events. When a person is not healthy, body temperature may become elevated as fever may be a common, natural response to infection. It may be helpful to know the expected body temperature of an individual so that a person can determine whether or not they are healthy. There have been many medical studies conducted to determine the average body temperature and the average fever temperature, or the range of these temperatures. For purposes of simplicity, the US Centers for Disease Control (CDC) advise that a person who has a temperature of 100.4 degrees Fahrenheit or above has a fever. That value of 100.4 degrees Fahrenheit comes from research published in 1868 by the German doctor Carl Reinhold August Wunderlich. Today, defining a fever as 100.4 degrees Fahrenheit may be considered a bit incorrect. However, for many infectious diseases, there may be a large difference between normal and fever temperatures, so this definition may be often useful anyway.

For COVID-19, people often have very mild symptoms, or symptoms that may be delayed. Even though fever may be a significant symptom for COVID-19, people with elevated temperatures are often considered asymptomatic if their fever fails to rise to 100.4 degrees Fahrenheit. However, for COVID-19, defining a fever as 100.4 degrees Fahrenheit may be hindering management of the pandemic. The reason may be that people believe that they are not sick when they are in fact sick. Because people with COVID-19 believe they are not sick, they interact with other persons and unintentionally infect them as well. COVID-19 may not be the only infectious disease that sometimes displays mild symptoms. Furthermore, unlike many other diseases, COVID-19 symptoms may be delayed. As a result, early warning of COVID-19 identification may be very important, yet it may be further hindered by defining a fever as 100.4 degrees Fahrenheit or higher.

The current state of the art may be insufficient to control the spread of the coronavirus and other infectious diseases. It is based on old, outdated data and people are grasping at non-medical, non-FDA approved, very expensive, and flashy technologies that do not reach the resolution for finding and identifying mild symptoms.

SUMMARY OF THE INVENTION

The Personal Warning Temperature (PWT) method of the present invention overcomes the deficiencies of prior-art methods for defining a fever, by creating an individualized personal warning temperature for every person using a set of their own body temperature measurements taken when they are healthy. It may be commonly known that normal body temperature varies by individual for a variety of reasons, perhaps including body weight, age and metabolism. As a result, fever, which is a body temperature higher than normal, also varies between individuals. For particular individuals, PWT uses statistical measures such as average (or mean) and standard deviation to define a personal warning temperature, which defines a fever for that specific person. PWT assumes normal body temperature taken over time may be normally distributed in the statistical sense, and it uses either the standard deviation or some multiple of standard deviation above the person's average normal temperature in order to define the personal warning temperature for the specific individual.

Displaying body temperatures in a time-based graph in any specific exemplary embodiment described herein facilitates understanding. Therefore, body temperature may be often part of an exemplary embodiment. Similarly, body temperature may be not necessary in order to calculate or display a personal channel of expected normal body temperatures in order to calculate or know a person's personal warning temperature. Displaying the channel also facilitates understanding and may be often displayed on a graph, along with the personal warning temperature of the individual.

Not only may a personal warning temperature be more accurate at identifying fever, it also triggers earlier because it may be generally lower than the traditional definition of 100.4 degrees Fahrenheit. By accurately defining a fever and identifying a fever earlier, people with the potential to infect others with disease can take appropriate action at an earlier date, in order to avoid or reduce the chances of infecting others.

Knowing your personal warning temperature, and specifically knowing when your body temperature measurement rises above your personal warning temperature, creates a new capability to provide early warning of possible illness, infectiousness, and ability to appropriately react in a timely manner, in order to help manage an epidemic, pandemic, or other health crisis with visibility that has never been known before. Your personal warning temperature may be more accurate and usually lower than the traditional definition of a fever such as 100.4 degrees Fahrenheit. This results in the feasibility of early warning when contracting a disease.

When displaying a person's body temperature data on a graph, it easy to see that, when healthy, the person's body temperature may be usually within a channel. It may be also relatively easy to determine when the person's body temperature rises above their personal warning temperature. The graph, with the personal warning temperature displayed, removes the need to remember their personal warning temperature.

In the case of COVID-19 and perhaps other infectious diseases, people with mild symptoms of the disease are not currently being detected when they are infectious, and thus they do not take precautions to avoid infecting others. Temperature screening devices are not identifying these people either because the devices are often set to trigger at 100.4 degrees, which may be the traditional definition of fever. PWT can more accurately and more quickly inform people when they are getting sick. If every person knew their personal warning temperature and monitored their body temperature daily, we would be in a much better position to manage the COVID-19 pandemic, and perhaps future pandemics.

In one embodiment presented herein, a method for providing an indication to recommend medical evaluation for a person includes providing a thermometer configured to measure a body temperature of a person, recording a first body temperature of the person measured with the thermometer at a first time of day, recording a second body temperature of the person measured with the thermometer at a second time of day, determining whether the second body temperature may be greater than the first body temperature, and providing an indication of a recommendation for medical evaluation of the person based on the second body temperature being greater than the first body temperature.

In another embodiment presented herein, a method for providing a recommendation for medical evaluation for a person includes providing a thermometer configured to measure a body temperature of a person, recording at least two of a series of first body temperatures of the person measured with the thermometer beginning at a first time of day, each of the first body temperatures of the series of first body temperatures being approximately 24 hours between each subsequent first body temperature measurement, calculating a mean first body temperature based on the series of first body temperatures, recording a second body temperature of the person measured with the thermometer at a second time of day, determining whether the second body temperature may be greater than the mean first body temperature, and providing an indication of a recommendation for medical evaluation of the person when the second body temperature may be determined to be greater than the mean first body temperature.

In another embodiment presented herein, a method for providing an indication to recommend medical evaluation for a person includes providing a thermometer configured to measure a body temperature of a person, recording at least two of a series of first body temperatures of the person measured with the thermometer beginning at a first time of day, each of the first body temperatures of the series of first body temperatures being approximately 24 hours between each subsequent first body temperature measurement, calculating a mean and a standard deviation of the series of first body temperatures of the person, determining a first time of day channel based on the computed standard deviation and centered around the mean of the series of the first body temperatures, wherein an upper boundary of the first time of day channel may be defined as a personal warning temperature of the person, recording a second body temperature of the person measured with the thermometer at a second time of day, determining whether the second body temperature may be greater than the personal warning temperature, and providing an indication of a recommendation for medical evaluation of the person based on the second body temperature when the second body temperature may be determined to be greater than the personal warning temperature.

BRIEF DESCRIPTION OF THE DRAWINGS

FIG. 8 shows one embodiment of a method for providing an indication to recommend medical evaluation for a person.

FIG. 9 shows another embodiment of a method for providing an indication to recommend medical evaluation for a person.

FIG. 10 shows another embodiment of a method for providing an indication to recommend medical evaluation for a person.

LIST OF REFERENCE NUMERALS FOUND IN THE DRAWINGS

Figure 1:
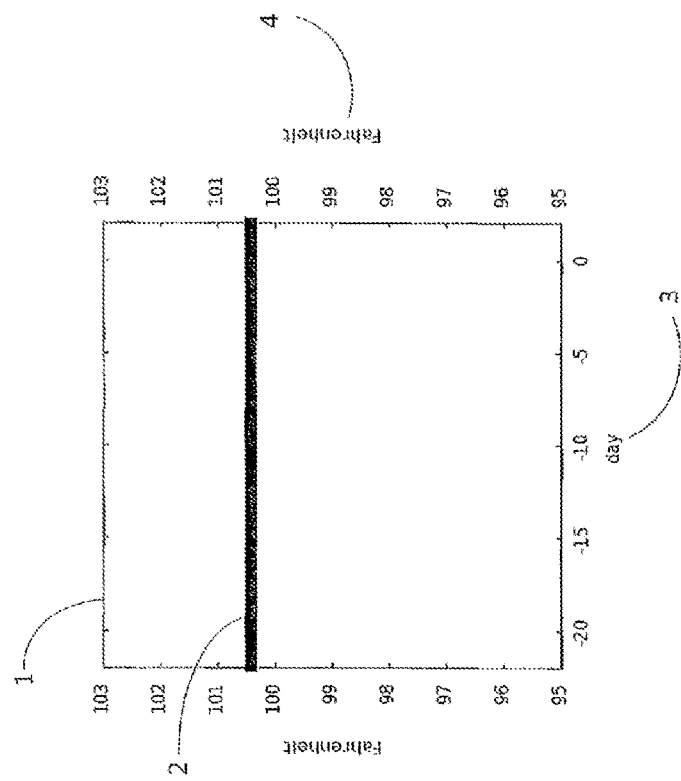
FIG. 1 provides a graphical representation of a temperature chart with the traditional fever temperature bar of 100.4 Fahrenheit.

Reference number 1 represents a graphical representation of temperatures taken by an individual, warning lines, and timelines.

Reference number 2 represents the standard used fever temperature of 100.4 line.

Reference number 3 may be a timeline in days.

Reference number 4 may be a temperature scale.

Reference number 20 are personal temperatures taken by an individual.

Reference number 31 represents the lower bound of the personal temperature standard deviation channel (SDC).

Reference number 32 represents the average personal temperature line (APT).

Reference number 33 represents the upper bound of the personal temperature standard deviation channel (SDC).

Reference number 34 represents the personal warning temperature (PWT) line.

Reference number 40 represents personal temperatures taken in the morning.

Reference number 41 represents personal temperatures taken in the evening.

Reference number 52 represents the new average personal temperature line (APT) based only on morning temperatures.

Reference number 54 represents the new personal warning temperature (PWT) line based on only morning temperatures.

Reference number 55 represents the change in the personal warning temperature line based on using only morning temperatures.

Reference number 56 represents the change in average personal temperature (APT) based only on evening temperatures.

Reference number 62 represents the new average personal temperature line (APT) base only on morning temperatures.

Reference number 64 represents the new personal warning temperature (PWT) line based on only evening temperatures.

Reference number 65 represents the change in the personal warning temperature line based using only evening temperatures.

Reference number 66 represents the change in average personal temperature (APT) based only on evening temperatures.

Reference number 70 represents time of day that the personal temperatures were taken.

Reference number 71 represents the average temperature based on time of day that temperature was taken.

Reference number 72 represents the personal warning temperature (PWT) line based on time of day that temperature was taken.

DETAILED DESCRIPTION OF THE EXEMPLARY EMBODIMENTS

In an exemplary embodiment of the Personal Warning Temperature (PWT) of the present invention, a healthy person's body temperature measurements are used to calculate an average (or mean) temperature, as well as a standard deviation. A multiplier (M1) of the standard deviation, may be used to define a channel of expected normal temperatures, which are defined by lower and upper temperature bounds which are above and below the average temperature by the same magnitude. The multiplier may be selected so that nearly all the healthy person's body temperatures are within the channel. It is well known that, for normally distributed data, such as healthy body temperature, appear to be, about 95% of measurements are within 2 standard deviations from the average. Therefore, in an exemplary embodiment, the channel multiplier M1 may be "2". Further, the person's personal warning temperature may be calculated using the average, the standard deviation, and another multiplier M2 such that the personal warning temperature may be M2 times the standard deviation above the average temperature, where M2 may be greater than M1. In another example, the channel multiplier may be "1," such that the standard deviation itself identifies the personal warning temperature.

In mathematical terms representing the exemplary embodiment, if the average body temperature may be A, and the standard deviation may be Sd, then the channel of expected normal temperatures for the healthy person may be defined by the lower bound, L, and the upper bound, U, and the personal warning temperature, W, may be defined as:

$$L = A - (M1 * Sd)$$

$$U = A + (M1 * Sd)$$

$$W = A + (M2 * Sd)$$

Many factors affect an individual's personal warning temperature such as time-of-day. An exemplary embodiment of PWT analyzes a healthy person's body temperature measurements in order to correct for time-of-day differences or interpret a body temperature measurement in order to take time-of-day into account.

Measurement methods also affect the body temperature value. For example, different thermometers may measure the body temperature differently, and, in addition to time-of-day, the location on the body that the temperature may be taken also affects the value. For the determination of fever, however, the particular measurement device utilized, and method may not be as important as making sure the temperature is measured in a systematic and consistent way every time, so that the set of measurements are precise, if not accurate. It may be not so important what the particular temperature level is. Instead, it may be only important to understand what the normal range of temperatures may be when healthy, have relatively small variation in the range of normal temperatures, and to know when the temperature rises above the normal range of values, indicating possible illness.

In an exemplary embodiment of PWT, a healthy person's body temperature measurements are plotted on a graph against the time of measurement along with the channel of expected normal temperatures and the personal warning temperature to facilitate understanding of body temperature history, and observe very clearly when a particular, future body temperature, rises above the personal warning temperature.

FIG. 1 illustrates a graph 1 of body temperature, measured in degrees Fahrenheit 4, with respect to time, measured in elapsed days 3, used in an embodiment. Other exemplary embodiments use other temperature or time units. There may be no body temperature illustrated in FIG. 1. However, the traditional definition of the fever threshold, 100.4 degrees Fahrenheit 2, may be shown.

Figure 2:
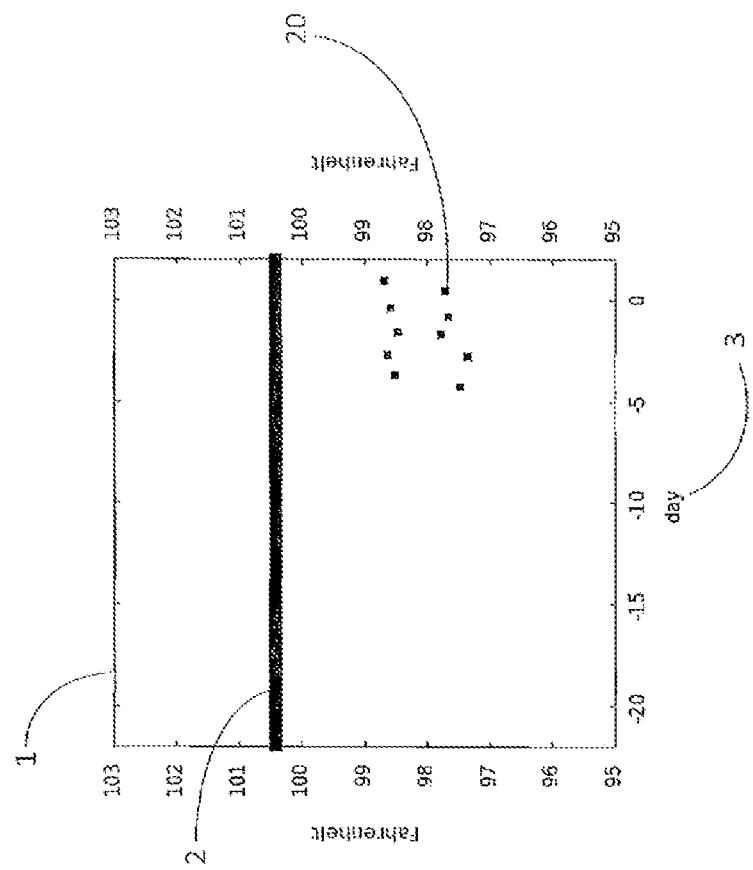
FIG. 2 provides a graphical representation of the results of an individual taking their personal temperature over time.

FIG. 2 illustrates the same graph 1 of FIG. 1 but now with some body temperature measurements 20 added for the temperature of an individual. PWT requires at least two body temperature measurements for the person, when healthy, to calculate non-trivial values for the average body temperature and standard deviation. In FIG. 2, there are ten body temperature measurements 20 taken at different times. In an exemplary embodiment, PWT uses a few body temperature measurements to calculate a non-changing channel and personal warning temperature. In another exemplary embodiment, the channel and personal warning temperature are calculated from all normal body temperature measurements, a moving time window of normal body temperature measurements, or some set of normal and/or all body temperature measurements.

Figure 3:
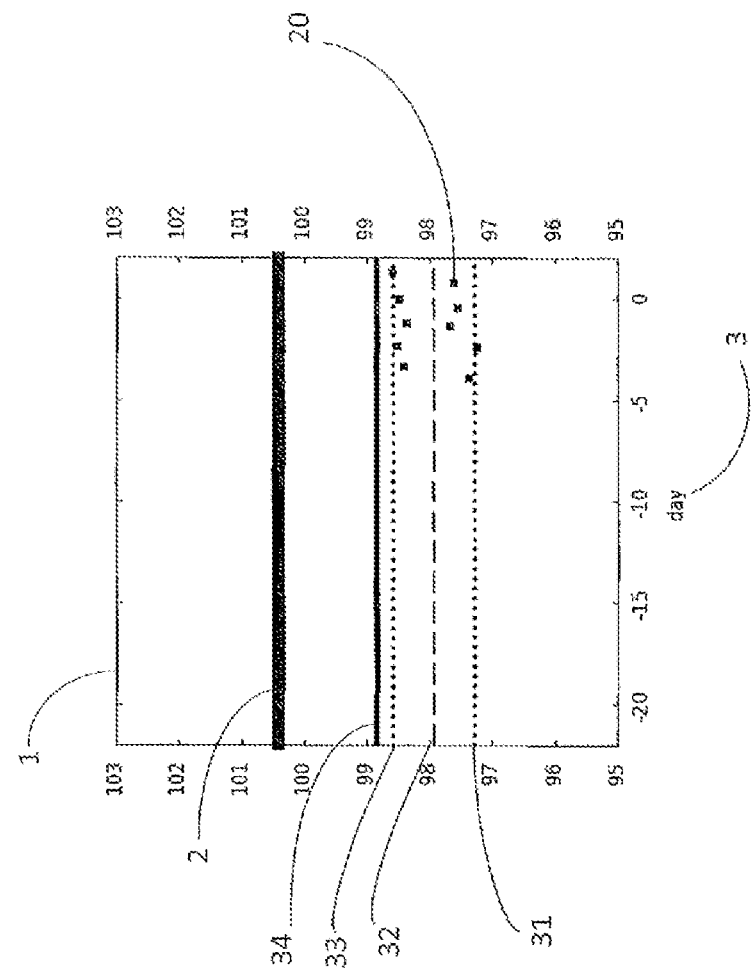
FIG. 3 shows a graphical representation of computing a personal temperature average, standard deviation channel, and personal warning temperature.

FIG. 3 illustrates the graph 1 of FIG. 1 with the average body temperature 32, the lower 31 and upper 33 bounds defining the expected normal temperature channel for the person when healthy, and the person's personal warning temperature 34.

Figure 4:
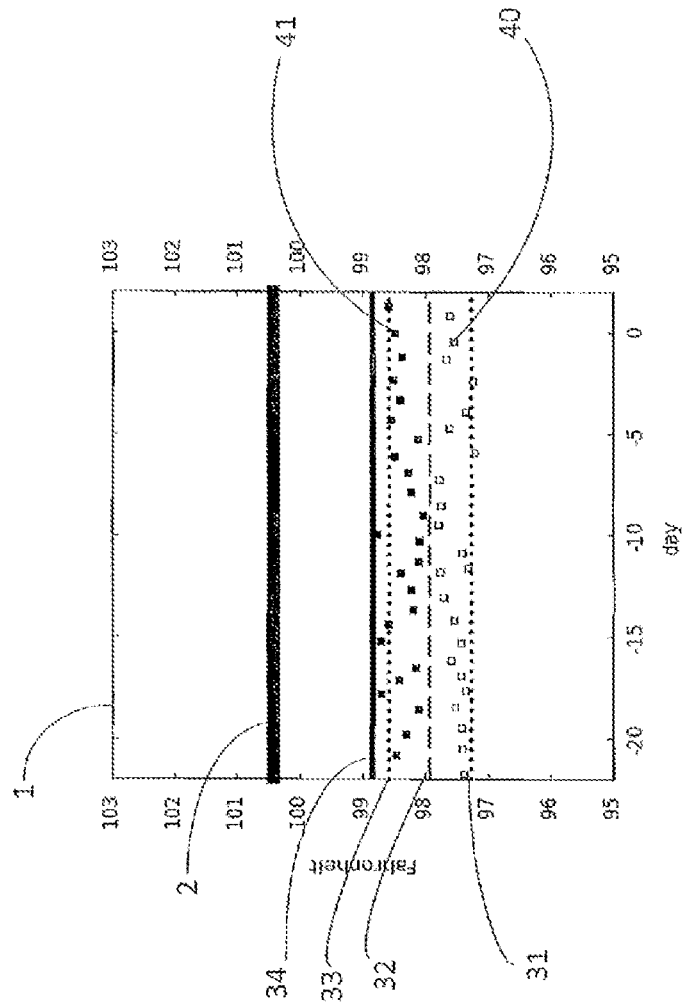
FIG. 4 shows a graphical representation of personal temperatures taken with the recorded time of day.

FIG. 4 illustrates the graph 1 of FIG. 1 with at least twenty days of the person's body temperature data, now distinguished by whether the temperature measurement was obtained in the morning 40 or evening 41. Because of circadian rhythm, body temperature may be often higher in the evening than it may be in the morning, assuming the person sleeps at night as most people do, (if not, then a different but explainable pattern can be observed). In an exemplary embodiment, the person measures body temperature at the same time each day to remove the time-of-day effects. In another exemplary embodiment, the person uses a morning hour each day. In yet another exemplary embodiment, the person uses an evening hour each day. In yet a further exemplary embodiment, the person uses both a morning hour and an evening hour.

Figure 5:
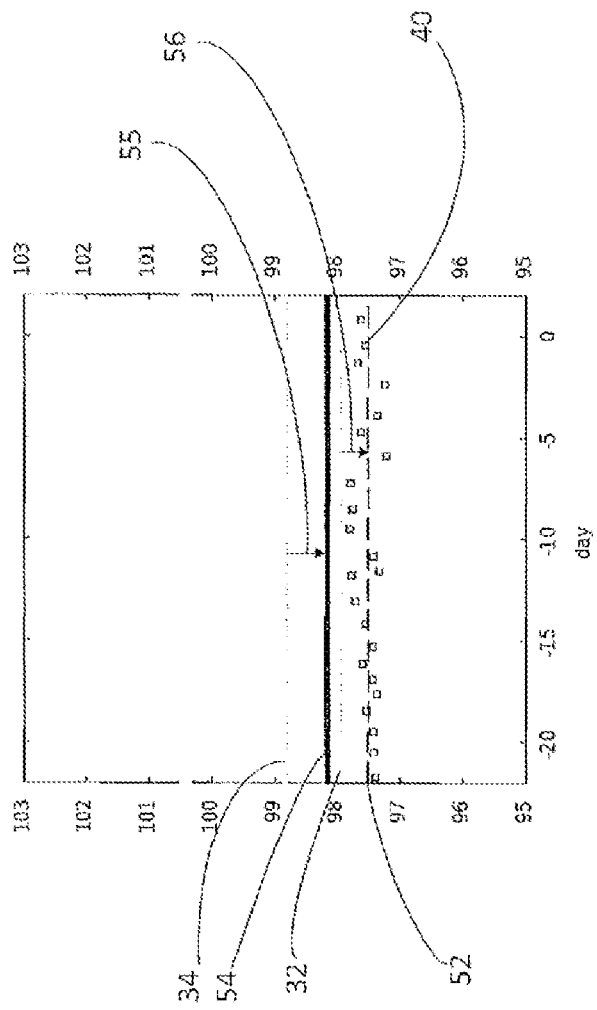
FIG. 5 shows a graphical representation of using personal temperatures collected and grouped in the morning, then computing averages, standard deviation, and a new lower personal warning temperature.

FIG. 5 shows only body temperature measurements 40 of the person for the morning hour. In an embodiment, the average 52 considering only morning-hour body temperature measurement 40 will be lower than the average considering all body temperature measurements 40 and 41 in FIG. 4. Similarly, the personal warning temperature 54, calculated using only morning-hour body temperature measurement 40 will be lower than the personal warning temperature 34 considering all body temperature measurements 40 and 41 in FIG. 4 and also shown in FIG. 5 as reference number 34, the difference being shown 55.

Figure 6:
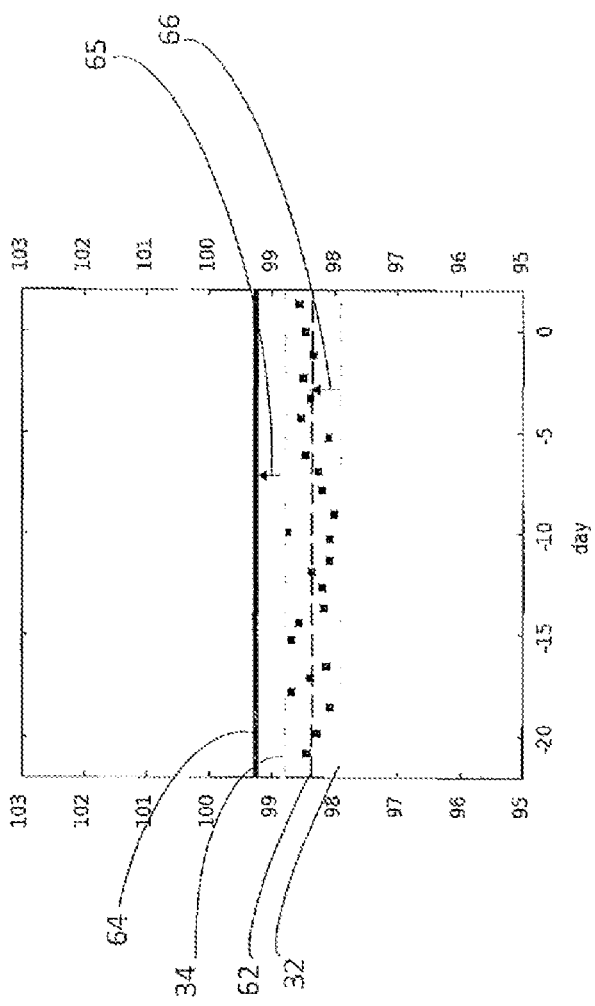
FIG. 6 shows a graphical representation of using personal temperatures collected and grouped in the evening, then computing averages, standard deviation, and a new higher personal warning temperature.

FIG. 6 shows only body temperature measurements 41 of the person for the evening hour. In an embodiment, the average 62 considering only evening-hour body temperature measurements will be higher than the average considering all body temperature measurements 40 and 41 in FIG. 4. Similarly, the personal warning temperature 64, calculated using only evening-hour body temperature measurement 41 will be higher than the personal warning temperature 34 considering all body temperature measurements 40 and 41 in FIG. 4 and also shown in FIG. 6, as reference number 34, the difference being shown 65.

Figure 7:
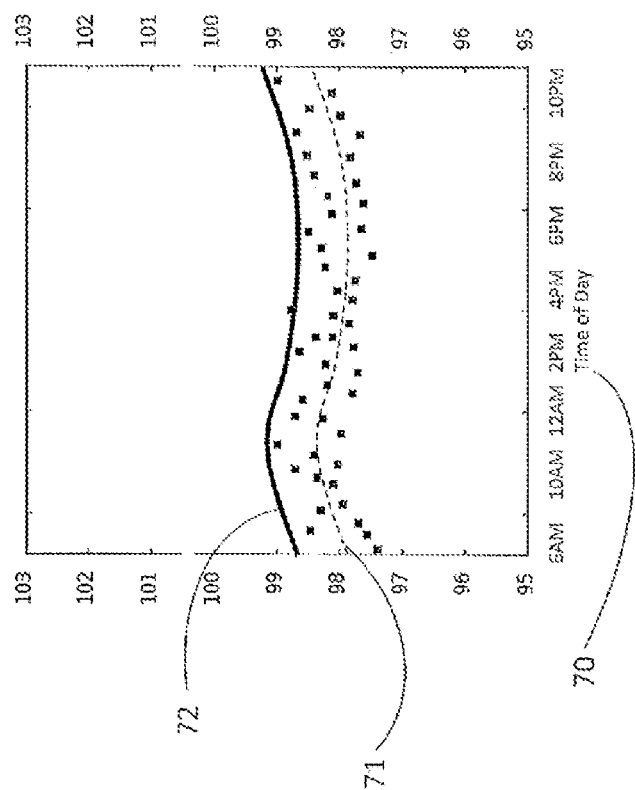
FIG. 7 shows a graphical representation of grouping an individual's personal temperatures by time of day modeling the normal temperature rise and fall thought the day and calculating the averages by time such as each hour and the new personal warning temperature based on time of day.

FIG. 7 shows the result of analyzing the person's body temperature measurements and correcting the channel and personal warning temperature for the effect of time-of-day variations expected for a person's body temperature. It may be commonly known that a person's body temperature varies throughout the day in a phenomenon known as circadian rhythm. There are two ways to address time-of-day expected variations in body temperature. In an embodiment, indicated by FIG. 7, the personal warning temperature and channel are modified to enable correct interpretation of the body temperature measured. In another exemplary embodiment, the measured body temperature may be adjusted for time-of-day expected variations and plotted on a graph with fixed values defining the channel and personal warning temperature.

There are several well-known methods for modeling the time-of-day expected variations in body temperature. For example, normal body temperature measurements can be used to find a mathematical function that fits the curve to the data when plotted on a graph. Alternatively, machine learning methods may be used to define a function.

There may be other identifiable factors that affect body temperature measurement in predictable ways. In an exemplary embodiment of PWT, a healthy person's body temperature measurements are analyzed, using machine learning or an equivalent technique, to determine how other factors affect body temperature and calculates a correction or method of interpreting body temperature in the context of those other factors.

Regarding circadian rhythm, body temperatures are normally higher in the evening and lower in the morning. If a person has an infection, the infection may manifest itself overnight, resulting in a higher morning body temperatures.

There may be different methods to determine if a person has a possible infection based on body temperature: (1) where a measured morning body temperature is higher that than of a measured evening body temperature taken the night before; and/or, (2) where a measured morning body temperature is beyond a safe multiplication factor of the standard deviation of measured morning body temperatures.

Both (1) and (2), above, indicate an abnormal condition which may be an indication of an early onset of COVID-19, another infectious disease, or a specific medical problem for the person.

Rapid test kits and Home test kits are readily available for use at home and while travelling. It is not common knowledge as to the particular time a person should perform a rapid test during an onset of a potential infection. Most tests are performed as a precaution, for example, for travel, or when experiences the onset of physical symptoms. One problem with this approach is, when someone manifests symptoms, they may already be in an infectious state. Thus, an earlier indication of infection is desired before symptoms present themselves.

Another problem is that precaution testing can be expensive with numerous and repetitive testing. Additionally, rapid tests are not reliable in early stages, such as in identifying COVID-19 when antigen presence is low or undetectable, yielding negative or inconclusive test results.

The following methods address these deficiencies by providing a back-stop for a person who tests negative, but still may have an abnormal temperature. An abnormal temperature should be viewed as a possible early development of an infection even with a negative rapid test.

Improved tests such as PCR-based COVID-19 tests are even more expensive than a rapid tests and generally do not provide immediate feedback. The below methods address the testing process started for a person in an earlier timeframe, while still providing a secondary indicator, temperature, to monitor during the serial testing process rather than simply relying on multiple negative test results which may not be accurate.

FIG. 8 illustrates another embodiment of a method 80 for providing an indication to recommend medical evaluation for a person. The method of FIG. 8 contemplates using the body temperature measurements as illustrated in FIG. 4, for example, taken in the morning 40 and taken in the evening 41, that is, body temperature measurements taken twice a day, at two different times of the day, and over a series of days.

The method of FIG. 8 includes providing 81 a thermometer configured to measure a body temperature of a person and recording 82 a first body temperature of the person measured with the thermometer at a first time of day. The method further includes recording 83 a second body temperature of the person measured with the thermometer at a second time of day. These body temperatures measured at different times of the day may correspond to a pair of sequential temperatures taken during an evening time, for example, data point indicated by reference number 41, and a subsequent data point taken during a morning time indicated by reference number 40.

The method further includes determining 84 whether the second body temperature may be greater than the first body temperature by comparing the values of the two body temperatures.

The method further includes providing 85 an indication of a recommendation for medical evaluation of the person based on the second body temperature being greater than the first body temperature.

The method further includes contemplating where the first time of day may be proximate a first time the person enters a sleep state. For example, a temperature taken of the person near a regular time close to when the person normally goes to sleep. The method further includes contemplating where the second time of day may be proximate a second time the person awakens from the sleep state. For example, another temperature taken of the person near a regular time after a person wakes up from a period of sleep.

The method further includes contemplating where the second body temperature may be measured with the thermometer in a similar manner as a first manner in which the thermometer may be used to measure the first body temperature. For example, the similar manner of measuring the second body temperature of the person may be defined as being at a same, similar or equivalent location either on the person, for example, a temporal or interaural thermal scan, or in the person, for example, an oral or anal thermal reading, to the first manner in which the thermometer may be used to measure the first body temperature.

The method further includes contemplating where the second time of day may be subsequent to the first time of day. For example, the first body temperature may be taken in the evening before the person goes to sleep, and the second body temperature may be taken in the morning after the person awakens from the same period of sleep.

The method further includes contemplating where the indication of the recommendation for medical evaluation includes prompting to administer a rapid diagnostic test on the person for detection of predetermined protein fragments within the person. For example, a rapid diagnostic test may include an antigen-based test designed to identify specific predetermined viral proteins of a target virus.

The method further includes contemplating where the indication of the recommendation for medical evaluation includes prompting to administer a diagnostic test on the person for one of a viral, bacterial or fungal infection. For example, a polymerase chain reaction (PCR) test designed to identify specific genetic material of a target source pathogen or abnormal cell sample of the person.

The method further includes contemplating where the indication of the recommendation for medical evaluation includes a prompt to administer any type of diagnostic test for a medical disease or condition associated with specific signs and symptoms, where the specific signs or symptoms my include a febrile condition of the person. For example, conditions where a person may exhibit a febrile condition, (pyrexia), may include, for example: infections caused by viruses, bacteria, protozoa, and fungus, (e.g., influenza, malaria, strep throat, SARS-CoV-2 virus, Valley fever); inflammatory conditions like arthritis and inflammatory bowel disease; cancerous tumors; systemic lupus erythematosus; heat stroke; and immune-mediated adverse reactions to vaccines.

The method may further include communicating a value of a personal warning temperature of the person, where the personal warning temperature of the person may be defined as the first body temperature of the person, the personal warning temperature being the value above which any subsequent measured body temperature triggers the provision of the indication of the recommendation for medical evaluation of the person.

FIG. 9 illustrates another method 90 for providing a recommendation for medical evaluation for a person. The method of FIG. 9 contemplates using the body temperature measurements as illustrated in FIG. 4, for example, taken in the morning 40 and taken in the evening 41, that is, body temperature measurements taken twice a day, at two different times of the day, and over a series of days.

The method of FIG. 9 includes providing 91 a thermometer configured to measure a body temperature of a person, and recording 92 at least two of a series of first body temperatures of the person measured with the thermometer beginning at a first time of day, each of the first body temperatures of the series of first body temperatures being approximately 24 hours between each subsequent first body temperature measurement. The method further includes calculating 93 a mean first body temperature based on the series of first body temperatures.

The method further includes 94 recording a second body temperature of the person measured with the thermometer at a second time of day and determining 95 whether the second body temperature may be greater than the mean first body temperature.

The method further includes providing 96 an indication of a recommendation for medical evaluation of the person when the second body temperature may be determined to be greater than the mean first body temperature.

The method further includes contemplating where the first time of day may be proximate a first time the person enters a sleep state. For example, a temperature taken of the person near a regular time close to when the person normally goes to sleep. The method further includes contemplating where the second time of day may be proximate a second time the person awakens from the sleep state. For example, another temperature taken of the person near a regular time after a person wakes up from a period of sleep.

The method further includes contemplating where each of the series of first body temperatures may be measured with the thermometer in a similar manner, where the similar manner of measuring each of the series of first body temperatures of the person may be defined as a same location either on the person, for example, a temporal or interaural thermal scan, or in the person, for example, an oral or anal thermal reading.

The method further includes contemplating where the second body temperature may be measured with the thermometer in a similar manner as a first manner in which the thermometer may be used to measure the series of first body temperatures, where the similar manner of measuring the second body temperature of the person may be defined as a same location either on the person, for example, a temporal or interaural thermal scan, or in the person, for example, an oral or anal thermal reading, to the first manner in which the thermometer may be used to measure the series of first body temperatures.

The method further includes contemplating where the second time of day may be subsequent to a last body temperature measurement of the series of first body temperatures taken at the first time of day.

The method may further include communicating a value of a personal warning temperature of the person, where the personal warning temperature of the person may be defined as the mean first body temperature of the person, the personal warning temperature being the value above which any subsequent measured body temperature triggers the provision of the indication of the recommendation for medical evaluation of the person.

FIG. 10 illustrates another method for providing an indication to recommend medical evaluation for a person. The method of FIG. 10 contemplates using the body temperature measurements as illustrated in FIG. 5, for example, taken in the morning 40, that is, body temperature measurements taken once a day and over a series of days.

The method of FIG. 10 includes providing 101 a thermometer configured to measure a body temperature of a person and recording 102 at least two of a series of first body temperatures of the person measured with the thermometer beginning at a first time of day, each of the first body temperatures of the series of first body temperatures being approximately 24 hours between each subsequent first body temperature measurement.

The method further includes calculating 103 a mean 52 and a standard deviation of the series of first body temperatures of the person.

The method further includes determining 104 a first time of day channel, (see for example, reference nos. 31 and 33 of FIGS. 3-4), based on the computed standard deviation and centered around the mean of the series of the first body temperatures, where an upper boundary 33 of the first time of day channel for the method illustrated in FIG. 101, may be defined as a personal warning temperature of the person.

The method further includes recording 105 a second body temperature of the person measured with the thermometer at a second time of day and determining 106 whether the second body temperature may be greater than the personal warning temperature.

The method further includes providing 107 an indication of a recommendation for medical evaluation of the person based on the second body temperature when the second body temperature may be determined to be greater than the personal warning temperature.

The method further includes contemplating where the first time of day and the second time of day are proximate a time the person awakens from a sleep state. For example, temperatures taken of the person near a regular time after a person wakes up from a period of sleep.

The method further includes contemplating where each of the series of first body temperatures may be measured in a similar manner with the thermometer, where the similar manner of measuring each of the series of first body temperatures of the person may be defined as a same location either on the person, for example, a temporal or interaural thermal scan, or in the person, for example, an oral or anal thermal reading.

The method further includes contemplating where the second body temperature may be measured in a similar manner with the thermometer as a first manner in which the thermometer may be used to measure the series of first body temperatures, where the similar manner of measuring the second body temperature of the person may be defined as a same location either on the person, for example, a temporal or interaural thermal scan, or in the person, for example, an oral or anal thermal reading, to the first manner in which the thermometer may be used to measure the series of first body temperatures.

The method further includes contemplating where the similar manner of measuring the second body temperature of the person may be defined as a same location either on the person, for example, a temporal or interaural thermal scan, or in the person, for example, an oral or anal thermal reading, to the first manner in which the thermometer may be used to measure the series of first body temperatures.

The method further includes contemplating where the second time of day may be subsequent to a last body temperature measurement of the series of first body temperatures at the first time of day.

The method further includes contemplating where the indication of the recommendation for medical evaluation includes a prompt to administer a rapid diagnostic test on the person for detection of predetermined protein fragments within the person. For example, a rapid diagnostic test may include an antigen-based test designed to identify specific predetermined viral proteins of a target virus.

The method further includes contemplating where the indication of the recommendation for medical evaluation includes a prompt to administer a diagnostic test for one of a viral, bacterial or fungal infection. For example, a polymerase chain reaction (PCR) test designed to identify specific genetic material of a target source pathogen or abnormal cell sample of the person.

The method further includes contemplating where the indication of the recommendation for medical evaluation includes a prompt to administer any type of diagnostic test for a medical disease or condition associated with specific signs and symptoms, where the specific signs or symptoms my include a febrile condition of the person.

The method may further include communicating a value of a personal warning temperature of the person, where the personal warning temperature of the person may be defined as the upper boundary of the first time of day channel, the personal warning temperature being the value above which any subsequent measured body temperature triggers the provision of the indication of the recommendation for medical evaluation of the person.

The foregoing description, for purpose of explanation, has been described with reference to specific arrangements and configurations. However, the illustrative examples provided herein are not intended to be exhaustive or to limit embodiments of the disclosed subject matter to the precise forms disclosed. Many modifications and variations are possible in view of the disclosure provided herein. The embodiments and arrangements were chosen and described in order to explain the principles of embodiments of the disclosed subject matter and their practical applications. Various modifications may be used without departing from the scope or content of the disclosure and claims presented herein.

The invention claimed is:

1. A method for providing an indication to recommend medical evaluation for a person, the method comprising:
   providing a thermometer configured to measure a body temperature of a person;
   recording a first body temperature of the person measured with the thermometer at a first time of day when the person enters a sleep state and taken at a first location of one of on or in the person;
   recording a second body temperature of the person measured with the thermometer at a second time of day when the person awakens from the sleep state and taken at the first location of one of on or in the person;
   determining that the second body temperature is greater than the first body temperature; and
   providing an indication of a recommendation for medical evaluation of the person based on the second body temperature being greater than the first body temperature, wherein the recommendation includes a prompt to administer to the person at least one of an antigen-based rapid diagnostic test, a polymerase chain reaction (PCR) diagnostic test, an infectious condition test, and one of a medical disease or condition diagnostic test.

2. The method of claim 1, wherein the second time of day is subsequent to the first time of day.

3. The method of claim 1, wherein the rapid diagnostic test detects predetermined protein fragments within the person.

4. The method of claim 1, wherein the test for the infectious condition is for one of a viral, bacterial or fungal infection.

5. The method of claim 1, wherein the test for the medical disease or condition is associated with specific signs and symptoms.

6. The method of claim 1, the method further comprising:
   communicating a value of a personal warning temperature of the person,
   wherein the personal warning temperature of the person is defined as the first body temperature of the person, the personal warning temperature being a temperature value above which any subsequent measured body temperature triggers the provision of the indication of the recommendation for medical evaluation of the person.

7. A method for providing a recommendation for medical evaluation for a person, the method comprising:

providing a thermometer configured to measure a body temperature of a person;

recording at least two of a series of first body temperatures of the person measured with the thermometer beginning at a first time of day when the person enters a sleep state, each of the first body temperatures of the series of first body temperatures being 24 hours between each subsequent first body temperature measurement and each of the first body temperatures of the series of first body temperatures taken at a first same location of one of on or in the person;

calculating a mean first body temperature based on the series of first body temperatures;

recording a second body temperature of the person measured with the thermometer at a second time of day when the person awakens from the sleep state and taken at the first same location of one of on or in the person;

determining that the second body temperature is greater than the mean first body temperature; and providing an indication of a recommendation for medical evaluation of the person when the second body temperature is determined to be greater than the mean first body temperature, wherein the recommendation includes a prompt to administer to the person at least one of an antigen-based rapid diagnostic test, a polymerase chain reaction (PCR) diagnostic test, an infectious condition test, and one of a medical disease or condition diagnostic test.

8. The method of claim 7, wherein the second time of day is subsequent to a last body temperature measurement of the series of first body temperatures at the first time of day.

9. The method of claim 7, the method further comprising:
communicating a value of a personal warning temperature of the person, wherein the personal warning temperature of the person is defined as the mean first body temperature of the person, the personal warning temperature being a temperature value above which any subsequent measured body temperature triggers the provision of the indication of the recommendation for medical evaluation of the person.

10. A method for providing an indication to recommend medical evaluation for a person, the method comprising:

providing a thermometer configured to measure a body temperature of a person;

recording at least two of a series of first body temperatures of the person measured with the thermometer beginning at a first time of day proximate at a time when the person enters a sleep state, each of the first body temperatures of the series of first body temperatures being 24 hours between each subsequent first body temperature measurement and each of the first body temperatures of the series of the series of first body temperatures taken at a first same location of one of on or in the person;

calculating a mean and a standard deviation of the series of first body temperatures of the person;

determining a first time of day channel based on the calculated standard deviation and centered around the mean of the series of the first body temperatures, wherein an upper boundary of the first time of day channel is defined as a personal warning temperature of the person;

recording a second body temperature of the person measured with the thermometer at a second time of day when the person awakens from the sleep state and taken at the first same location of one of on or in the person;

determining that the second body temperature is greater than the personal warning temperature; and providing an indication of a recommendation for medical evaluation of the person based on the second body temperature when the second body temperature is determined to be greater than the personal warning temperature, wherein the recommendation includes a prompt to administer to the person at least one of an antigen-based rapid diagnostic test, a polymerase chain reaction (PCR) diagnostic test, an infectious condition test, and one of a medical disease or condition diagnostic test.

11. The method of claim 10, wherein the second time of day is subsequent to a last body temperature measurement of the series of first body temperatures at the first time of day.

12. The method of claim 10, wherein the rapid diagnostic test detects predetermined protein fragments within the person.

13. The method of claim 10, wherein the test for the infectious condition on the person for one of a viral, bacterial or fungal infection.

14. The method of claim 10, wherein the test for the infectious condition on the person for one of a viral, bacterial or fungal infection.

15. The method of claim 10, the method further comprising:
communicating a value of the personal warning temperature of the person, wherein the personal warning temperature of the person is defined as the upper boundary of the first time of day channel, the personal warning temperature being a temperature value above which any subsequent measured body temperature triggers the provision of the indication of the recommendation for medical evaluation of the person.

* * * * *